(12) United States Patent
Qi et al.

(10) Patent No.: US 9,012,159 B2
(45) Date of Patent: Apr. 21, 2015

(54) CELL BASED SCREENING ASSAYS FOR THE TRIGLYCERIDE SYNTHESIS PATHWAY

(75) Inventors: Jian-Shen Qi, Chalfont, PA (US); Wensheng Lang, Lower Gwynedd, PA (US); Margery A. Connelly, Lansdale, PA (US)

(73) Assignee: Janssen Research & Development, LLC, Raritan, NJ (US)

( * ) Notice: Subject to any disclaimer, the term of this patent is extended or adjusted under 35 U.S.C. 154(b) by 895 days.

(21) Appl. No.: 12/683,527

(22) Filed: Jan. 7, 2010

(65) Prior Publication Data

US 2010/0196930 A1 Aug. 5, 2010

Related U.S. Application Data

(60) Provisional application No. 61/149,841, filed on Feb. 4, 2009.

(51) Int. Cl.
| | | |
|---|---|---|
| *G01N 33/567* | (2006.01) | |
| *G01N 33/50* | (2006.01) | |
| *C12Q 1/48* | (2006.01) | |
| *G01N 33/60* | (2006.01) | |
| *G01N 33/92* | (2006.01) | |

(52) U.S. Cl.
CPC .............. *G01N 33/5038* (2013.01); *C12Q 1/48* (2013.01); *G01N 33/60* (2013.01); *G01N 33/92* (2013.01)

(58) Field of Classification Search
None
See application file for complete search history.

(56) References Cited

FOREIGN PATENT DOCUMENTS

| WO | WO 2004/069809 A1 | 8/2004 |
| WO | WO 2005/108597 A2 | 11/2005 |
| WO | WO 2006/067071 A1 | 6/2006 |
| WO | WO 2007/147023 A1 | 12/2007 |
| WO | WO 2008/148868 A1 | 12/2008 |

OTHER PUBLICATIONS

Lee S.W. et al. Inhibition of Diacylglycerol Acyltransferase by Alkamides Isolated from the Fruits of *Piper longum* and *Piper nigrum*, J. Agric. Food Chem., 2006, vol. 54, pp. 9759-9763.*
Guo W. et al., Octanoate Inhibits Triglyceride Synthesis in 3T3-L1 and Human Adipocytes, J. Nutr., 2003, vol. 133, pp. 2512-2518.*
Timms A.R. et al., Modification of Lofland's colorimetric semiautomated serum triglyceride determination, assessed by an enzymatic glycerol determination, Journal of Lipid Research, 1968, vol. 9, 675-680.*
Hutchins P.M. et al., Separation of cellular nonpolar neutral lipids by normal-phase chromatography and analysis by electrospray ionization mass spectrometry, J. Lipid Res., 2008, vol. 49, pp. 804-813.*
U2: Mancuso D.J. et al., Dramatic Accumulation of Triglycerides and Precipitation of Cardiac Hemodynamic Dysfunction during Brief Caloric Restriction in Transgenic Myocardium Expressing Human Calcium-independent Phospholipase A2gamma, The Journal of Biological Chemistry, 2007, vol. 282, No. 12, pp. 9216-9227.*
V2: Zhang D. et al., Mitochondrial dysfunction due to long-chain Acyl-CoA dehydrogenase deficiency causes hepatic steatosis and hepatic insulin resistance, PNAS, Oct. 23, 2007, vol. 104, No. 3, pp. 17075-17080.*
Agarwal A.K. et al., Functional characterization of human 1-acylglycerol-3-phosphate acyltransferase isoform 8: Cloning, tissue distribution, gene structure, and enzymatic activity, Archives of Biochemistry and Biophysics, 2006, vol. 449, pp. 64-76.*
Cases, S. et al. "Cloning of DGAT2, a Second Mammalian Diacylglycerol Acyltransferase, and Related Family Members", The Journal of Biological Chemistry, Jul. 31, 2001, vol. 276, No. 42, U.S., pp. 38870-38876.
Cases, S. et al. "Identification of a Gene Encoding an Acy CoA:diacylglycerol Acyltransferase, a Key Enzyme in Triacylglycerol Synthesis", Proc. National Academy Sci, Oct. 1998, vol. 95, pp. 13018-13023.
Choi, C.S. et al. "Suppression of Diacylglycerol Acyltransferase-2 (DGAT2), but Not DGAT1, with Antisense Oligonucleotides Reverses Diet-Induced Hepatic Steatosis and Insulin Resistance", Journal of Biological Chemistry, Aug. 3, 2007, vol. 282, No. 31, pp. 22678-22688.
Liu, Y. et al. "Knockdown of Acyl-CoA:diacylglycerol Acyltransferase 2 with Antisense Oligonucleotide Reduces VLDL TG and ApoB Secretin in Mice", Biochimica et Biophysica Acta, vol. 1781, (2008), pp. 97-104.
Smith, S.J. et al. "Obesity Resistance and Multiple Mechanisms of Triglyceride Synthesis in Mice Lacking Dgat", Nature Genetics, vol. 25, May 2000, pp. 87-90.
Stone, S.J. et al. "Lipopenia and Skin Barrier Abnormalities in DGAT2-Deficient Mice", Journal of Biological Chemistry, vol. 279, No. 12, Mar. 19, 2004, pp. 11767-11776.
International Search Report from PCT/US2010/022981 dated Apr. 22, 2010 (3 pages).
Lewis et al., "Disordered Fat Storage and Mobilization in the Pathogenesis of Insulin Resistance and Type 2 Diabetes," *Endocrine Reviews*. 2002; 23(2):201-229.
Magkos et al., "Reproducibility of stable isotope-labeled tracer measures of VLDL-triglyceride and VLDL-apolipoprotein B-100 kinetics," *J. Lipid Res.*, 2007; 48:1204-1211.
Malloy et al., "A risk factor for atherosclerosis: triglyceride-rich lipoproteins," *Adv. Intern Med.*, 2001; 47:111-136.
Zhu et al., "Effect of gemfibrozil on apolipoprotein B secretion and diacylglycerol acyltransferase activity in human hepatoblastoma (HepG2) cells," *Atherosclerosis*, 2002; 164: 221-228.

* cited by examiner

*Primary Examiner* — Satyendra Singh
(74) *Attorney, Agent, or Firm* — Bernard F. Plantz; Johnson & Johnson (57) ABSTRACT

A method for identifying a compound which modulates the activity of acyl-coA: diacylglycerol acyltransferase comprises the steps of contacting a stable isotope labeled fatty acid with cells in either presence or absence of the compound, extracting the cells with isopropyl alcohol, and determining the level of a stable isotope labeled triglyceride in the presence or absence of the compound; wherein a change in the level of the stable isotope labeled triglyceride indicates that the compound modulates the DGAT activity.

9 Claims, 8 Drawing Sheets

CELL BASED SCREENING ASSAYS FOR THE TRIGLYCERIDE SYNTHESIS PATHWAY

CROSS REFERENCE TO RELATED APPLICATION

This application claims benefit of U.S. Provisional Application Ser. No. 61/149,841 filed Feb. 4, 2009 which is incorporated herein by reference in its entirety and for all purposes.

BACKGROUND OF THE INVENTION

1. Field of the Invention

A method is provided for simultaneously detecting lipids and phosphatidate intermediates in cells incubated with stable-isotope labeled fatty acids. The method may be used for screening compounds that modulate triglyceride biosynthesis in a high-throughput format.

2. Description of the Related Art

Triglyceride or triacylglycerol is a major transport source and energy storage in eukaryotes. Triglyceride is synthesized from a glycerol molecule and three fatty acid molecules. Each of the fatty acid molecules is attached, via an ester bond, to each of three hydroxyl groups of the glycerol molecule. Triglyceride, as many neutral lipids, contains fatty acid molecules in various chain lengths with a common length of 16, 18, or 20 carbons.

The two major biosynthetic pathways of triglyceride are the glycerol-3-phosphate pathway, which exists predominately in liver and adipose tissue, and a monoacylglycerol pathway, which exists predominately in the intestine. The glycerol-3-phosphate pathway, generating more than 90% of triglyceride in liver, is illustrated below:

Wherein FA-CoA is fatty acid CoA, GPAT is glycerol-3-phosphate acyltransferase, AGPAT is 1-acylglycerol-3-phosphate-O-acyltransferase, PAP is phosphatidic acid phosphatase and DGAT is acyl-coA: diacylglycerol acyltransferase.

The final step of the glycerol-3-phosphate biosynthetic pathway can be catalyzed by either DGAT1 or DGAT2 (Cases et al. 1998, Proc Natl Acad Sci USA 95:13018; Cases et al. 2001 J Biol Chem 276:38870). Although DGAT1 and DGAT2 both convert diglyceride to triglyceride, they do not share similarity in either nucleotide or amino acid sequences. It has been reported that knockout mice lacking DGAT1 (Dgat1$^{-/-}$) do not display obvious changes in triglyceride metabolism in the liver (Smith et al. 2000, Nat Genet. 25:87). In addition, knockout mice lacking DGAT2 (Dgat2$^{-/-}$) display severely reduced triglyceride content in the liver (Stone et al. 2004, J Biol Chem 279:11767). Further, studies have shown that suppression of DGAT2 with antisense oligonucleotides reduces hepatic triglyceride content in rodents (Chol et al. 2007, J Biol Chem 282:22678; Liu et al. 2008, Biochim Biophy Acta 1781:97) and reverses diet-induced hepatic steatosis and insulin resistance in rats (Chol et al. 2007, J Biol Chem 282:22678). These studies suggest that DGAT1 and DGAT2 function differently in triglyceride biosynthesis. Therefore, specific targeting of either DGAT1 or DGAT2 may provide benefit in modulating triglyceride with limited toxicity.

Disorder or imbalance in triglyceride metabolism has been associated with pathogenesis and increased risk for obesity, metabolic syndrome, type II diabetes, nonalcoholic fatty liver disease and coronary heart disease (Lewis et al. 2002, Endocrine Reviews 23:201; Malloy and Kane 2001, Adv Intern Med 47:111). Therefore, compounds that modulate enzymatic activity within the triglyceride biosynthetic pathway, including DGAT1 and DGAT2, may be useful as potential therapeutic targets for metabolic diseases.

The radioactive substrates and a thin-layer chromatography have been widely used to monitor triglyceride synthesis (Stone et al. 2004, J Biol Chem 279:11767; Zhu et al. 2002, Atherosclerosis 164:221). Stone et al. labels triglycerides with $^3$H-glycerol in primary hepatocytes and detects the radioisotope-labeled triglycerides using thin-layer chromatography and radio image analysis (Stone et al. 2004, J Biol Chem 279:11767). Similarly, Zhu et al. labels triglycerides with $^3$H-oleic acid in human hepatocarcinoma cells and detects the labeled triglycerides using thin-layer chromatography (Zhu et al. 2002, Atherosclerosis 164:221).

Recently, Magkos et al. uses the mass spectrometry technology to detect neutral lipids (Magkos et, al. 2007, J Lipid Research 48: 1204). Magkos et al. administers 1,1,2,3,3-$^2$H-glycerol and 2,2-$^2$H-palmitate in vivo, and extracts very low density lipoprotein triglycerides from plasma by chloroform/methanol and ultracentrifugation. Magkos et al. detects labeled glycerol and methylated palmitate released from triglycerides using a gas chromatography-mass spectroscopy system (Magkos et al. 2007, J Lipid Research 48:1204). Magkos et al. does not detect intact triglyceride, i.e. specific triglyceride molecules, nor different intermediates in the triglyceride pathways.

As far as applicants know, the existing assays do not monitor or detect the intermediates including lysophosphatidic acid, phosphatidic acid and diacylglycerol generated during the triglyceride biosynthesis. Also, the existing assays require additional extraction procedures and labor-intensive detection techniques. Further, these methods have limited throughput and are difficult to be adapted for high-throughput format for screening large numbers of compounds. Thus, there is still a need to develop a method for analyzing triglyceride biosynthesis and identifying compounds, which modulate the triglyceride pathway in a high-throughput format.

SUMMARY

An object of the present application is to provide a method for identifying a compound which inhibits the activity of acyl-coA: diacylglycerol acyltransferase (DGAT). The method comprises the steps of contacting a stable isotope labeled fatty acid with cells in either presence or absence of the compound, extracting the cells with isopropyl alcohol, determining the level of a stable isotope labeled triglyceride in the presence of the compound and determining the level of a stable isotope labeled triglyceride in the absence of the compound; wherein a change in the level of the stable isotope labeled triglyceride is indicative of the compound inhibiting the DGAT activity.

Another object of the present application is to provide a method for measuring the activity of an enzyme involved in triglyceride synthesis. The method comprises the steps of contacting a stable isotope labeled fatty acid molecule with cells, extracting the cells with isopropyl alcohol and detecting the presence of a stable isotope labeled lysophosphatidic acid, phosphatidic acid, diacylglycerol or triglyceride.

According to the present application, the stable isotope labeled fatty acid may be $^{13}C_{18}$-oleic acid. Also according to the present application, the stable isotope labeled triglyceride may be detected by a liquid chromatographic-mass spectrophotometer system.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The present application provides a method that overcomes the limitations of existing assays for analyzing triglyceride synthesis. The method described herein uses a stable isotope-labeled fatty acid in a reaction mixture, such that the reaction mixture contains cells, growth medium, and the stable isotope labeled fatty acid. The method described herein may also be used for screening a compound, which modulates the enzymes involved in triglyceride synthesis. For screening purpose, the reaction mixture may further comprise a modulator of the enzyme involved in triglyceride, such as DGAT in the glycerol-3-phosphate pathway.

Any prokaryotic and eukaryotic cells may be used for the method described herein. Adipocytes, hepatoma cells, cancer cells, or leukemia cells are preferred, for example 3T3-L1, HUH7, FU5AH, THP-1, HepG2, C3HT101/2, McA-RH7777, MCF7, A549, and RAW264.7. The cells may be obtained through commercial source or isolated by a commonly known method. For example, methods isolating hepatocytes may be found in Berry and Friend, 1969, J Cell Biol 43: 506, and adipocytes may be found in Green et al. 1990, J Biol Chem 265:5206. The leukocytes may be isolated from a biological sample taken from an individual, such as any body fluid or tissue sample. Any body fluid includes but not limited to serum, plasma, lymph, cystic fluid, urine, stool, cerebrospinal fluid (csf), and acitic fluid. Suitable tissue samples include whole blood, semen, saliva, tears, urine, fecal material, sweat, buccal smears, skin, and biopsies of specific organ tissues such as muscle or nerve tissue and hair. The analysis of activity of glycerol-3-phosphate pathway in biological samples may be useful as biomarker for monitoring response of a patient to treatment with drugs for metabolic diseases.

The cells may be maintained in regular growth medium, such as Dulbecco's modified eagles medium, minimum essential medium, RPMI and the like. Some cells may be induced or differentiated prior to being analyzed. A person skilled in the art will recognize that suitable medium and conditions are needed for maintaining and/or inducing specific cell lines. For example, 3T3-L1 preadipocyte cells may be maintained in Dulbecco's modified eagles medium and induced by induction medium to become mature adipocyte cells.

Any fatty acid molecule labeled with stable isotope may be used for the method described herein. The term of "stable isotope" as used herein generally refers to an isotope molecule that is not radioactive, including $^{13}C$ or $^2H$. The stable isotope labeled fatty acids may be synthesized in-house or obtained commercially. The preferred fatty acid molecules contain chain lengths ranging from $C_{10}$ to $C_{20}$, such as monodesaturated $C_{16}$ and $C_{18}$. The fatty acid molecules may be labeled, uniformly or partially, by either $^{13}C$ or $^{2}H$; for example, uniformly labeled $^{13}C$-14:0, $^{13}C$-16:1, $^{13}C$-16:0, $^{13}C$-18:2, $^{13}C$-18:1, and $^{13}C$-18:0, $^{2}H_{29}$-16:1, $^{2}H_{31}$-16:0, $^{2}H_{33}$-18:1, $^{2}H_{35}$-18:0 or partially labeled $^{2}H$ with a mass shift of at least 4 amu. In one embodiment, the labeled molecule is $^{13}C_{18}$-oleic acid. The stable isotope labeled fatty acid may be incorporated into each step of the pathway resulting in newly synthesized intermediates or the product labeled with stable isotope.

A variety of other reagents also can be included in the reaction mixture. These include reagents such as salts, buffers, neutral proteins (e.g., albumin), detergents, etc. that may be used to facilitate enzymatic activities. Such a reagent may also reduce non-specific or background interactions of the reaction components. Other reagents that improve the efficiency of the assay such as inhibitors, antimicrobial agents and the like may also be used.

Prior to initiation of the method for analyzing triglyceride biosynthesis, endogenous fatty acids are depleted by culturing cells with charcoal-treated serum or serum-free medium for an appropriate period of time. Then, the stable isotope labeled fatty acid such as $^{13}C_{18}$-oleic acid is added to the reaction. The cells are then washed with phosphate buffered saline and the lipid molecules are extracted with isopropyl alcohol. Other solvent systems, including hexane, chloroform, heptane, acetone, dimethyl sulfur oxide, and butanol, may be used for extracting lipid molecules as well.

The newly synthesized labeled lipid intermediate or product may be detected by any method suitable for detecting the presence of an isotope or measuring molecule mass of an isotope molecule. For example, thin-layer chromatography and mass spectrometry may be used. In one embodiment, a liquid chromatography-mass spectrometry (LC-MS) system is used to detect and quantify the newly synthesized lipid molecules containing the stable isotope labeled acyl chain. In addition, multiple labeled lipid molecules may be detected simultaneously. In one embodiment, a mass spectrometry system is modified for simultaneous analysis of multiple neutral lipids including mono-, di- and tri-acylglycerols and phosphatidate intermediates in the glycerol-3-phosphate pathway. The modification includes a run with electron spray ionization in positive and negative switching without pre-column derivatization in a mass spectrometry system. Simultaneous detection of multiple lipids may also be done in one analytical run.

Once labeled lipid molecules are detected, their approximate levels may be determined by a normalized concentration method. By way of example, the normalized concentration is determined by an internal standard of 1,3-dipalmitoyl-2-stearoyl-glycerol-d5 (PSP-d5). The relative response of triolein or newly synthesized lipid molecules to those of the internal standard in a sample is obtained and used for quantification. It is found herein that about 1 µM of PSP-d5 solution in isopropyl alcohol could be used directly for extracting the lipid molecules. In addition, the ammonium adduct ion of PSP-d5 at m/z 858.0 could be used for ion extraction and integration. A skilled person in the art can determine the specific levels of detected molecules by other commonly used methods.

To evaluate whether a compound is able to modulate triglyceride synthesis, the compound is added to a reaction mixture which comprises stable isotope labeled fatty acid, growth medium and cells. The reaction is incubated for appropriate time, for example, about 10 minutes to about 24 hours. The reaction is extracted for lipid molecules with isopropyl alcohol and analyzed using a LC-MS system. When the levels of labeled triglyceride in the reaction with a compound is significantly different from those of the reaction without the compound, it is likely the compound modulates the enzyme involved in triglyceride synthesis. The term 'significantly different', as used herein, means the difference would lead a person skilled in the art to believe that the triglyceride synthesis is modulated. The difference in the levels of labeled triglyceride may be at least 10%, preferably at least 25%.

Compounds encompass numerous chemical classes, although typically they are organic compounds. Also, compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. Compounds can comprise cyclic carbon or heterocyclic structure and/or aromatic or polyaromatic structures substituted with one or more of the above-identified functional groups. Compounds also can be biomolecules such as peptides, saccharides, fatty acids, sterols, isoprenoids, purines, pyrimidines, derivatives or structure analogs of the above, or combinations thereof and the like. Where the compound is a nucleic acid, the compound typically is a DNA or RNA molecule, although modified nucleic acids having non-natural bonds or subunits are also contemplated.

Compounds may be obtained from a wide variety of sources including libraries of synthetic or natural compounds. For example, numerous means are available for random and direct synthesis of a wide variety of organic compounds and biomolecules, including expression of randomized oligonucleotides, synthetic organic combinatorial libraries, phage display libraries of random peptides, and the like. Compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam, 1997, Anticancer Drug Des. 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents may be subjected to directed or random chemical modifications such as acylation, alkylation, esterification, amidification, etc. to produce structural analogs of the agents. Compounds can be selected randomly or can be based on existing compounds that bind to and/or modulate the DGAT activity. Therefore, a source of candidate agents is libraries of molecules based on the known DGAT modulators, in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing DGAT modulators. The terms "modulator", "modulate" and the like, as used herein, refer to a compound that either increases or decreases the activity of the enzyme. When the enzyme activity is decreased in the presence of the compound, the compound is referred to as an inhibitor. When the enzyme activity is increased in the presence of the compound, the compound is referred to an activator.

By way of example, the effects of DGAT modulators Compounds 1 and 2 on the triglyceride synthesis are evaluated using the method described herein. Compounds 1 and 2 have been disclosed in WO2008148868 and WO2004069809, which are incorporated by reference in their entirety. Compound 1, DGAT 1 inhibitor, is N-[2,6-Dichloro-4-(pyrrolidin-1-ylmethyl)phenyl]-4-(4-{[(4-methoxyphenyl)acetyl]amino}phenyl)piperazine-1-carboxamide. Compound 1 has the molecular weight of 596.55 and the structure of Compound 2, DGAT 2 inhibitor, is dimethyl 1-[cyclohexyl (3,4-dichlorophenyl)methyl]-2-thioxo-2,3-dihydro-1H-imidazole-4,5-dicarboxylate. Compound 2 has the molecular weight of 457.38 and the structure of When a LC-MS system is used for detecting the labeled triglyceride molecules, a suitable solution is needed for extracting the lipid molecules from the reaction mixture. Some organic solvents such as hexane, chloroform/methanol, DMSO or the like, may not be compatible with the reversed-phase LC-MS detection system. Therefore, when hexane, chloroform/methanol, DMSO or the like are used for extraction, additional steps are needed to remove such organic solvent and reconstitute the extracted reaction mixture with a compatible solvent system prior to detection with the LC-MS system.

It is found herein that the use of isopropyl alcohol is compatible with the LC-MS system; therefore it can be used for extracting and delivering lipid molecules without additional steps. The one step extraction increases the efficiency and enables the high-throughput format, desired for screening large numbers of compounds and identifying compounds, which modulate triglyceride synthesis.

The term "high throughput" refers to an assay design that allows easy screening of multiple samples simultaneously and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known in the art that as miniaturization of plastic molds and liquid handling devices are advanced, or as improved assay devices are designed, greater numbers of samples may be performed using the design of the present invention.

In one embodiment, the cells are cultured and analyzed in the micro-titer plates containing a plurality of wells such as 96- or 386-well plates. The plates are loaded to a detection system such as LC-MS or the like, which reads the reaction in each well of each plate to generate numeric data. The method as described herein is also useful for evaluating the cellular activity of enzymes involved in triglyceride synthesis, including DGAT, GPAT, AGPAT, and PAP. The method may also be used for screening compounds that modulate enzyme activity in triglyceride biosynthesis in a high-throughput format. Further, the method of the present application may be used as a diagnostic assay for determining metabolic activity of triglyceride synthesis in isolated cells from human subjects.

EXAMPLE 1

Preparation of Cell Lines

The 3T3-L1 mouse preadipocyte cells were maintained in Dulbecco's Modified Eagles Medium (DMEM) with 10% fetal bovine serum (FBS). Cells were seeded in 96-well plates. Two days post confluency, the medium was changed to induction medium with IBMX, insulin, and dexamethasone (Adipolysis kit, Cayman Chemical Company). Three days after induction, the medium was changed to insulin medium (Adipolysis kit, Cayman Chemical Company). Five days after induction, the medium was replaced with fresh insulin medium for 2 days. Human hepatoma cell line HUH7 was maintained in DMEM with 10% FBS, 4.5 g/L D-glucose. Rat hepatoma cell line FU5AH was maintained in Minimum Essential Medium Eagle (MEM) with 5% FBS. The hepatoma cells were plated in 96 well plates and used at 80% confluence. Human breast cancer cell line MCF7 cells were maintained in DMEM with 10% FBS, 4.5 g/L D-glucose. Human monocytic leukemia cell line THP-1 was maintained in RPMI medium with 10% FBS and used at $5 \times 10^5$ cells/ml.

EXAMPLE 2

Stable Isotope Labeling of the Triglyceride Synthetic Pathway

The HUH7 cells or the differentiated 3T3-L1 cells were incubated with DMEM with 10% charcoal-stripped FBS (Gibco) in 5% $CO_2$ at 37° C. for overnight. The FU5AH cells were incubated with MEM with 5% charcoal-stripped FBS in 5% $CO_2$ at 37° C. for overnight. About 100 µl of 300 µM $^{13}C_{18}$-oleic acid (SIGMA) precomplexed with 0.5% fatty acid free BSA (SIGMA) were added to the cell suspension in 5% $CO_2$ at 37° C. for 0, 30, 60, 120 and 180 minutes. Then the cells were washed once with phosphate buffered saline and extracted with 100 µl of isopropyl alcohol. After incubating at room temperature for 10 minutes, the extraction was transferred to a glass vial and detected for labeled lipid molecules using the LC-MS system.

The LC-MS detection was conducted with Agilent 1100 Liquid Chromatographic system (Agilent Technologies, Palo Alto, Calif.) interfaced with a Micromass triple-quadrupole Quattro Micro mass spectrophotometer (Waters, Milford, Mass.) through a Z-spray electrospray ion source (ESI). Separation of the metabolites was performed on an Eclipse XDB-C8 column (2.1×50 mm, particle size=3.5 µm). Mobile Phase A, 50 mM ammonium formate in isopropanol-water (3:7), and mobile phase B, 10 mM ammonium formate in isopropanol-water (9:1) were used for a gradient elution as following: 20-100% Mobile Phase B for 1 min, hold 100% Mobile Phase B for 4 min, return to 20% Mobile Phase B for 0.1 min, then post run time of 4.5 min. The flow rate was 0.5 ml/min. The resulting LC eluate was introduced into the mass spectrometer at 0.25 ml/min with a 1:2 split. The mass spectrometer was operated in positive and negative ion switching mode. Nitrogen was used as nebulizing gas, desolvation gas and cone curtain gas. The source parameters for the MS system were: capillary voltage, 3.1 kV; cone voltage, 20 V ($ESI^+$) and 15V ($ESI^-$); extractor, 2V; RF lens, 0.1V; source temperature, 120° C.; desolvation temperature, 300° C.; LM1, HM1, LM2 or HM2 resolutions 15; ion energy 1, 1.0; entrance & exit, 15. The MassLynx software version 4.1 was used for system control and data processing.

Figure 1:
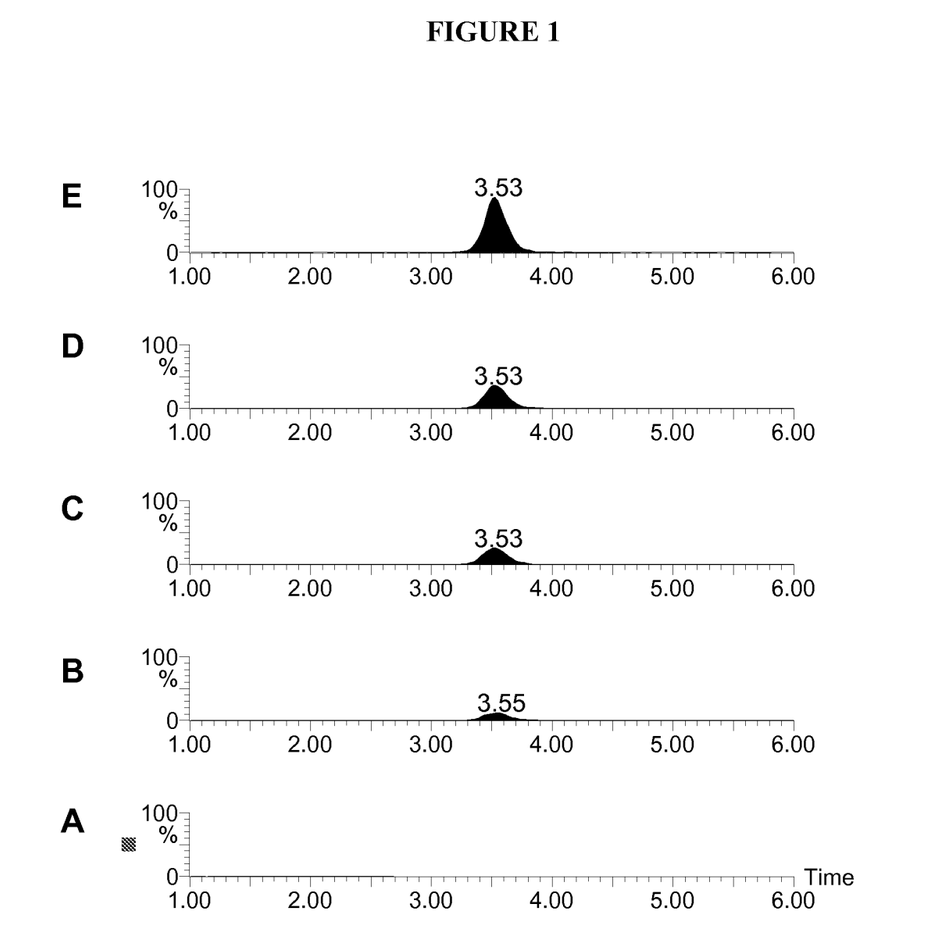
FIG. 1. Extracted ion chromatograms of $^{13}C$ labeled triolein with 3 oleoyl-$^{13}C_{18}$ side chains showing the total incorporation of free $^{13}C_{18}$-oleic acid into triglyceride in the FU5AH cells at 0 minute (A), 30 minutes (B), 60 minutes (C), 120 minutes (D), and 180 minutes (E).
Figure 2:
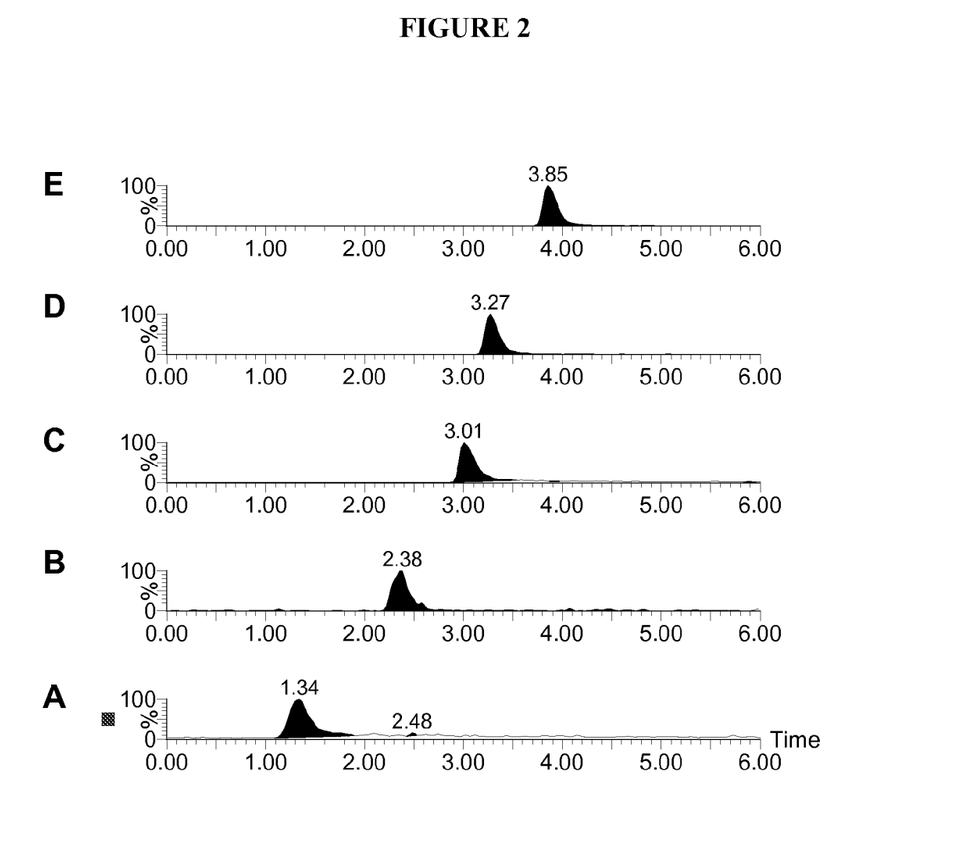
FIG. 2. Simultaneous monitoring of intermediates and final product of triolein synthesis using LC-MS positive and negative ion switching: (A) oleoyl lysophosphotidate, (B) monooleoyl glycerol, (C) dioleoyl phosphatidyate, (D) dioleoyl glycerol, and (E) trioleoyl glycerol.

In the FU5AH cells, the incorporation of $^{13}C_{18}$-oleic acid into the glycerol-3-phosphate pathway was determined by the presence of $^{13}C_{18}$-triolein (FIG. 1). The levels of the $^{13}C_{18}$-triolein were increased with the incubation time by comparing to the area under curve at 30 minutes, 60 minutes, 120 minutes, and 180 minutes (FIG. 1). Further, a LC-MS method for simultaneous detecting intermediates of oleoyl lysophosphatidate, 2-mono-oleoyl glycerols, 1,2-dioleoyl-sn-glycero-3-phosphatidate, 1,2-dioleoyl-sn-glycerol, and a final product of trioleoyl-sn-glycerol using positive and negative ion switching was newly developed herein (FIG. 2). This indicates that stable isotope labeling in combination with the detection of LC-MS system can be used for simultaneous detection of various steps of the triglyceride biosynthesis in the cells.

EXAMPLE 3

Evaluating Compounds which Modulate DGAT activity

For evaluating compounds which modulate activity of DGAT1 or DGAT2, HUH7 or 3T3-L1 cells were preincubated with about 0, 0.03, 0.1, 0.3, 1, 3, or 10 µM Compounds 1 or 2 for about 10 minutes at 37° C. in 100 µl serum free medium with 0.05% DMSO. The control is the cells incubated with 100 µl serum free medium with 0.05% DMSO, in the absence of any compound, for about 10 minutes at 37° C. About 100 µl of 600 µM $^{13}C_{18}$-oleic acid precomplexed with 1.0% fatty acid free BSA were added to the cell suspension. After incubation at 37° C. for about 90 minutes, cells were extracted and detected as described in Example 2.

Figure 3:
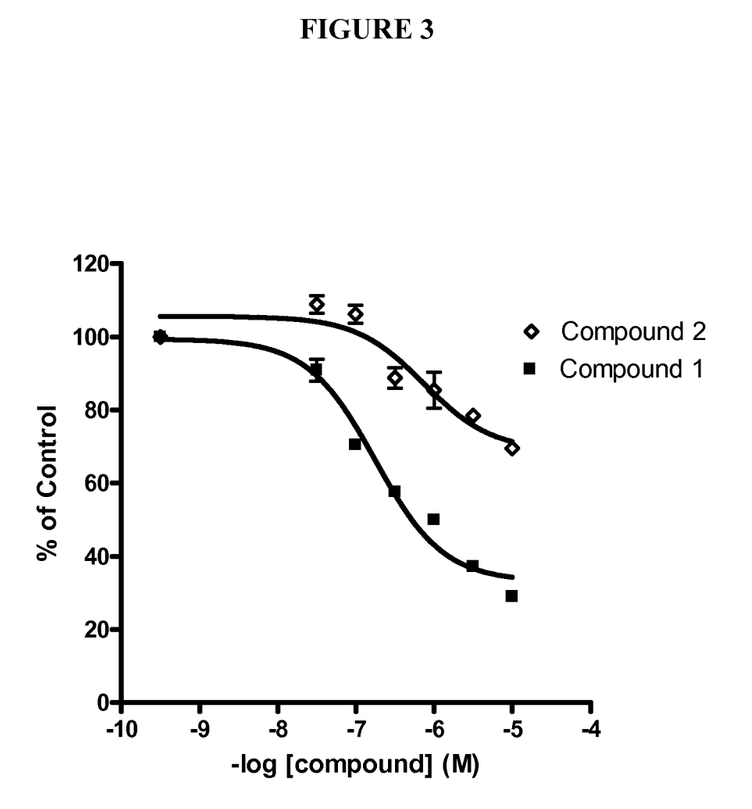
FIG. 3. Evaluation of effect of DGAT1 and DGAT2 inhibitors on the newly synthesized triolein with three oleoyl-$^{13}C_{18}$ chains in the HUH7 hepatocytes.
Figure 4:
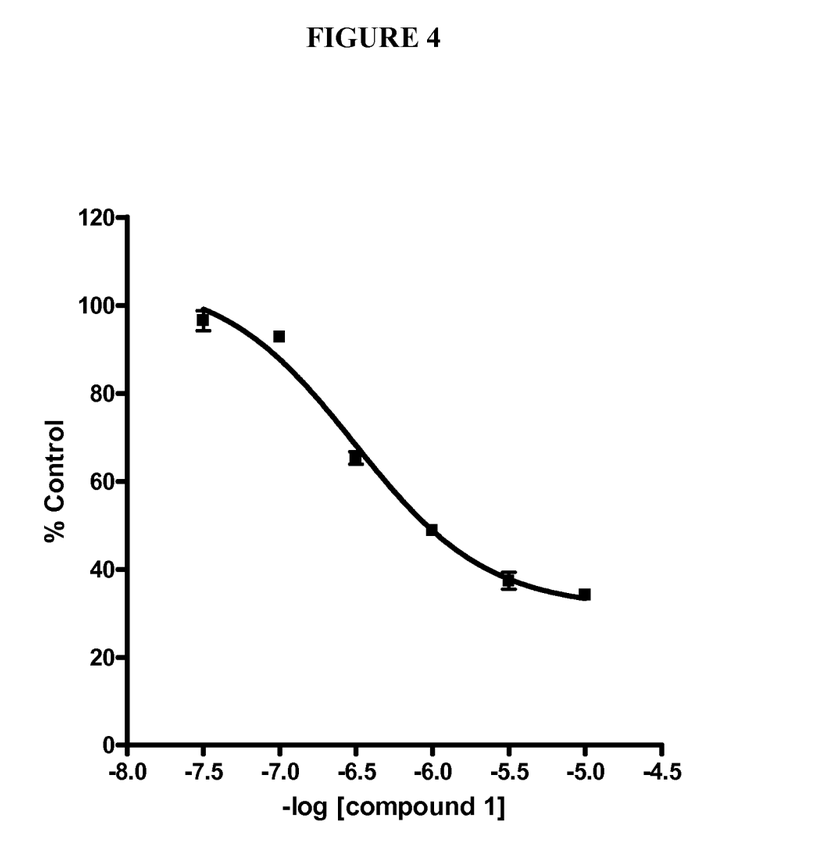
FIG. 4. Evaluation of a DGAT1 inhibitor on the newly synthesized triolein with three oleoyl-$^{13}C_{18}$ chains in the 3T3-L1 differentiated adipocytes.
Figure 5:
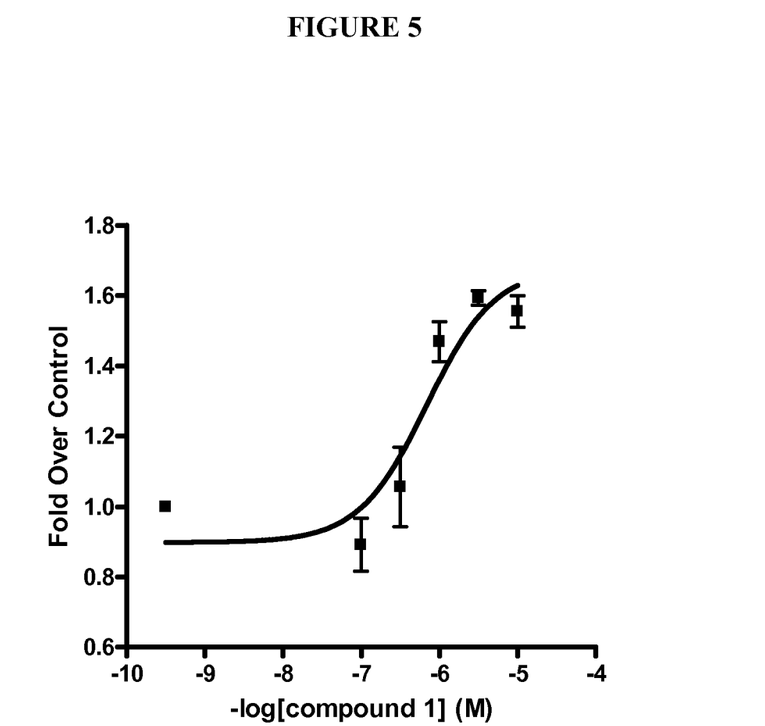
FIG. 5. Transient increase of diglyceride with two oleoyl-$^{13}C_{18}$ chains upon DGAT1 inhibition in the HUH7 hepatocytes.

The effects of Compounds 1 and 2 on the triglyceride biosynthesis were shown in FIGS. 3 to 6. Both HUH7 and differentiated 3T3-L1 cell lines had reduced levels of the newly synthesized $^{13}C_{18}$-triolein in the presence of Compound 1. In the HUH7 cell line, the levels of $^{13}C_{18}$-triolein in the cells incubated with 10 µM Compound 1 were about 30% of those of the control, and the levels of $^{13}C_{18}$-triolein in the cells incubated with 10 µM Compound 2 were about 75% of those of the control (FIG. 3). Additionally, a transient increase of $^{13}C_{18}$-oleoyl-diglyceride was detected in the HUH7 cells incubated with Compound 1 (FIG. 5). These results suggest that the HUH7 cells have both functional DGAT1 and DGAT2 enzymes converting $^{13}C_{18}$-diolein to $^{13}C_{18}$-triolein.

In the differentiated 3T3-L1 cell line, the levels of $^{13}C_{18}$-triolein in the cells incubated with about 10 µM Compound I were about 33% of those of the control (FIG. 4). The results suggest, in the differentiated 3T3-L1 cells, the majority of $^{13}C_{18}$-triolein is synthesized by DGAT1.

Figure 6:
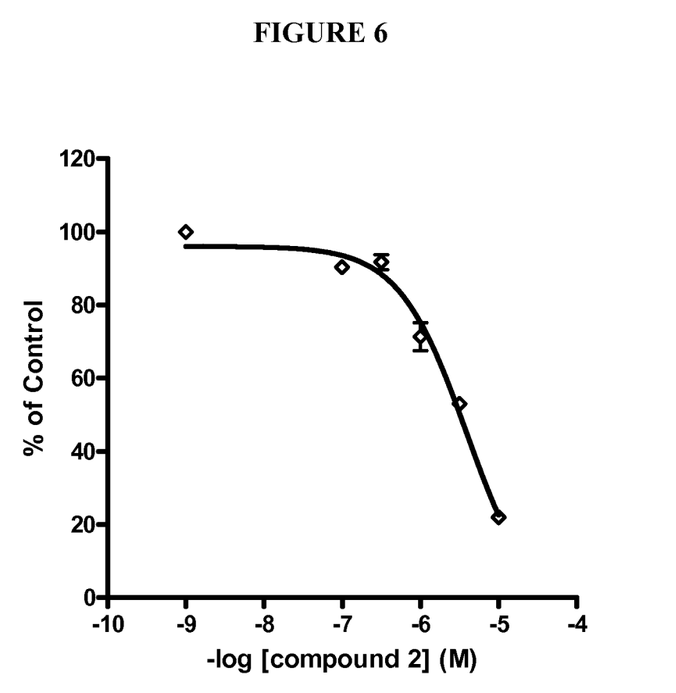
FIG. 6. Evaluation of a DGAT2 inhibitor on the newly synthesized triolein with three oleoyl-$^{13}C_{18}$ chains in MCF7 cells.

Next, the effects of Compound 2 in MCF7 cells were evaluated. The MCF7 cells were seeded in DMEM with 10% FBS, 4.5 g/L D-glucose in a 96-well culture plate for 24 hours. Cells at or near confluence were incubated with about 150 µl of serum-free DMEM with 0.15% fatty acid free BSA for 1 hour. Then about 3 µl of Compound 2 in DMEM containing 3% DMSO was added to a final concentration of about 0, 0.1, 0.3, 1, 3, 10 µM. After incubation at 37° C. for 15 minutes, the plate was drained. Then the cells were incubated with 150 µl of 100 µM $^{13}C_{18}$-oleic acid precomplexed with 0.15% fatty acid free BSA and about 3 µl of compound 2 in DMEM containing 3% DMSO for about 3 hours at 37° C. The cells were extracted with about 100 µl of isopropyl alcohol, followed by LC-MS detection as described above. As shown in FIG. 6, the levels of $^{13}C_{18}$-triolein in the cells incubated with Compound 2 were about 80% of those of the control. The results suggest in MCF7 cells, as used hereby, the majority of $^{13}C_{18}$-triolein is synthesized by DGAT2.

Figure 7:
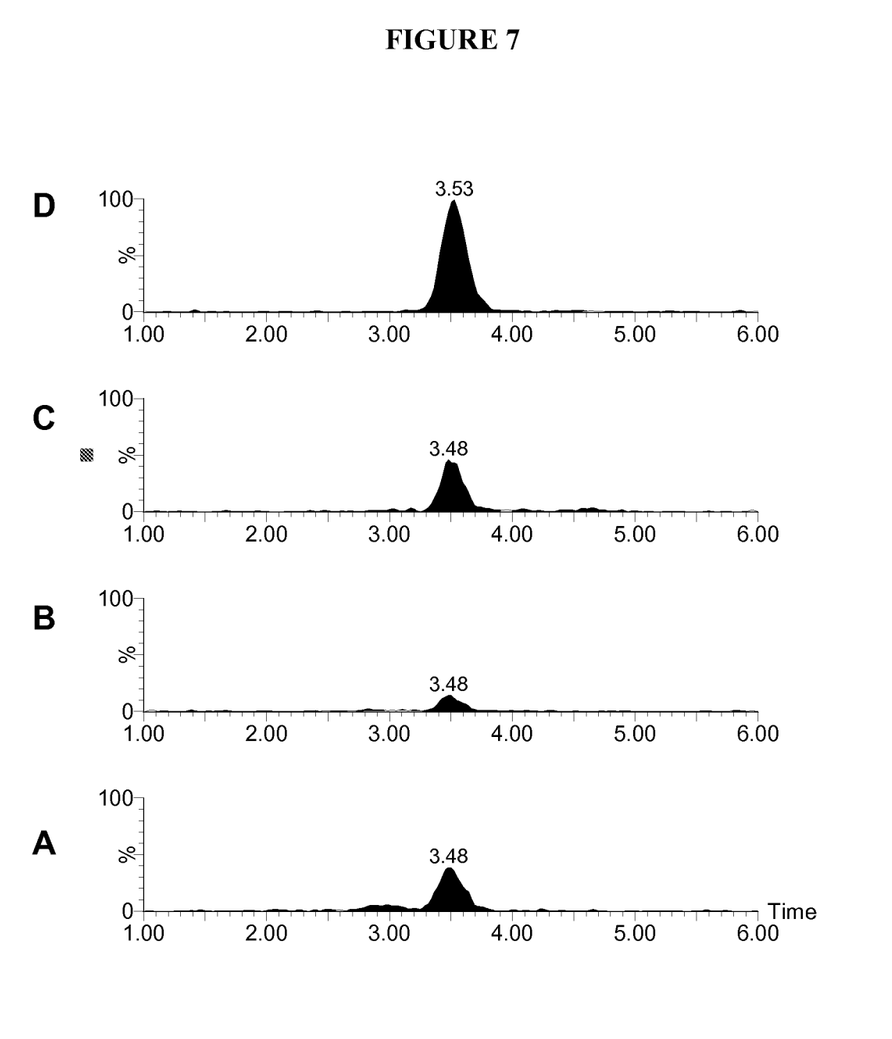
FIG. 7. Simultaneous detection of triolein with one, two, and three oleoyl-$^{13}C_{18}$ side chains in the FU5AH cells after cultured with oleic-$^{13}C_{18}$ acid for 60 minutes: (A) endogenous triolein detected at m/z 903.0, (B) $^{13}C_{18}$-triolein at m/z 921.0, (C) $^{13}C_{36}$-triolein at m/z 939.0, and (D) $^{13}C_{84}$-triolein at m/z 957.0.

As the generation of $^{13}C_{18}$-triolein with three labeled fatty acid chains involving other enzymes in the glycerol-3-phosphate pathway, additional experiments were conducted to detect the presence of labeled intermediates. The FU5AH cells were incubated with $^{13}C_{18}$-oleic acid for 60 minutes and analyzed using simultaneous detection as described in Example 2. As shown in FIG. 7, triolein with one, two, and three $^{13}C_{18}$-oleoyl side chains appear as labeled molecules with molecular mass at m/z 921.0, 939.0 and 957.0, respectively.

The results of Example 3 indicate that the differentiated adipocyte and HUH7 cells can be used for screening compounds, which modulate DGAT1 activity. On the other hand, the MCF7 cells can be used for screening compounds, which modulate DGAT2 activity. Further, MCF7, adipocyte and hepatoma cells can be used for screening compounds, which modulate other enzymes, including GPAT, AGPAT, or PAP, which are involved in the triglyceride biosynthesis such as the glycerol-3-phosphate pathway.

EXAMPLE 4

Detection of Triglyceride Biosynthesis in Leukocytes

To examine whether the triglyceride biosynthesis exists in the leukocytes, the THP-1 cells were incubated with serum free RPMI and incubated at 37° C. for 2 hours. About 200,000 cells were centrifuged for 5 min at 500×g. About 300 µl of 300 µM $^{13}C_{18}$-oleic acid (SIGMA) precomplexed with 0.5% fatty acid free BSA (SIGMA) in RPMI was added to the cell pellet. The cells were incubated with the labeled molecule at 37° C. for 2 hours and extracted with isopropyl alcohol as described above.

Figure 8:
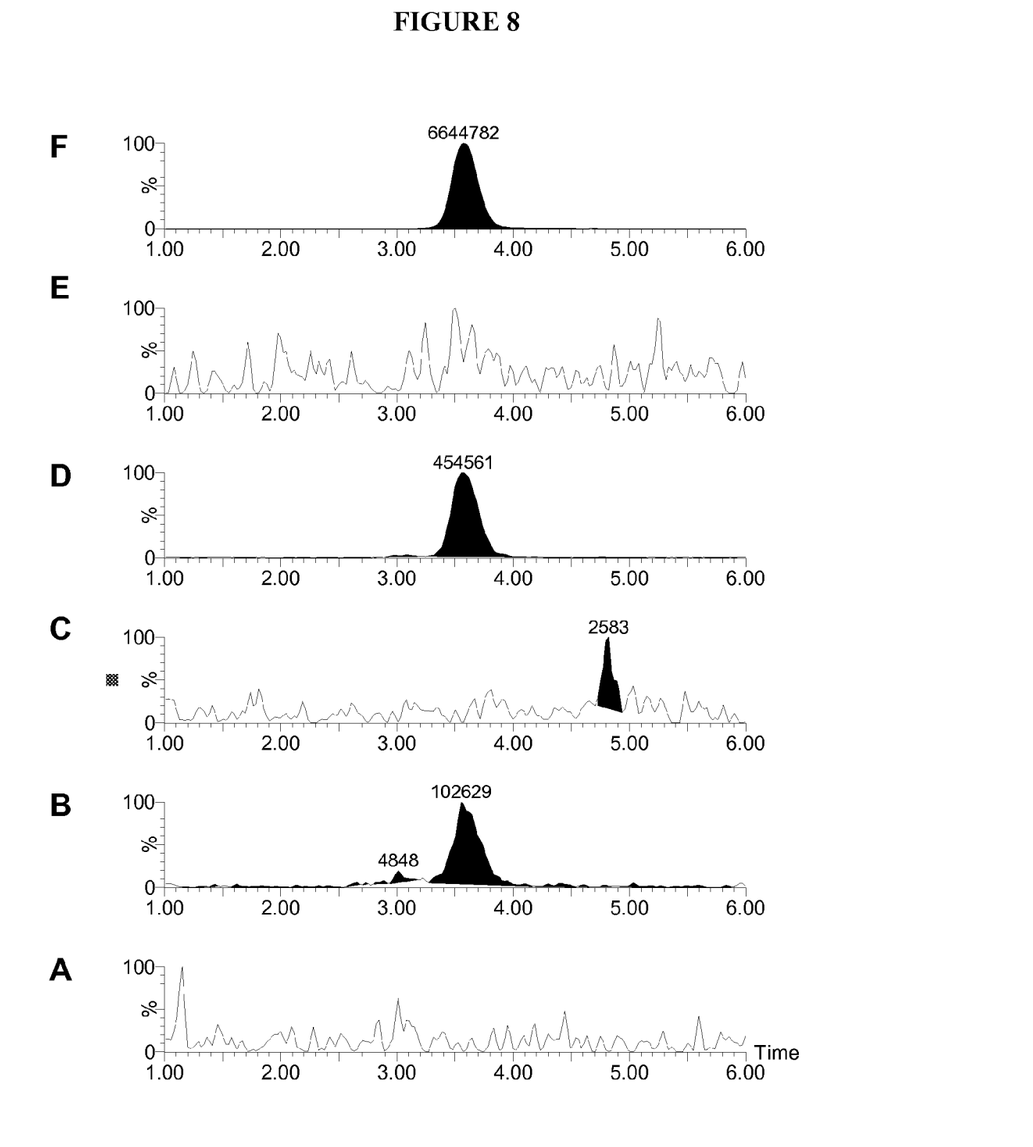
FIG. 8. Simultaneous detection of triolein with one, two, and three oleoyl-$^{13}C_{18}$ side chains in the THP-1 monocytes incubated with or without $^{13}C_{18}$-oleic acid for 120 minutes. (A) $^{13}C_{18}$-triolein was not detected at m/z 921.0 in the absence of $^{13}C_{18}$-oleic acid, (B) $^{13}C_{18}$-triolein was observed in the presence of $^{13}C_{18}$-oleic acid, (C) $^{13}C_{36}$-triolein was not detected at m/z 939.0 in the absence of $^{13}C_{18}$-oleic acid, (D) $^{13}C_{36}$-triolein was observed in the presence of $^{13}C_{18}$-oleic acid, (E) $^{13}C_{54}$-triolein was not detected at m/z 957.0 in the absence of $^{13}C_{18}$-oleic acid, and (F) $^{13}C_{54}$-triolein was observed in the presence of $^{13}C_{18}$-oleic acid.

As shown in FIG. 8, a newly synthesized $^{13}C_{1-8}$-triolein was detected in the THP-1 cells cultured with the labeled oleic acid but not in the control cells cultured without the labeled oleic acid. When the THP-1 cells were cultured with $^{13}C_{18}$-oleic acid for about 120 minutes, the triolein with one or two $^{13}C_{18}$-oleoyl side chains was detected as labeled molecules with molecular mass at m/z 921.0 and 939.0, respectively.

The detection of the partially labeled triolein indicates that the method of the present application can be used to detect cellular activity of AGPAT, PAP, or DGAT. Further, the method described herein can be used to detect newly synthesized triglyceride in isolated cells hence may be used as a diagnostic assay to determine the metabolic activity of triglyceride biosynthesis.

All references cited in this section are incorporated by reference entirety.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A high-throughput method for identifying a compound which inhibits the in vivo activity of acyl-coA: diacylglycerol acyltransferase (DGAT) in cells, comprising the steps of:
   a. contacting a stable isotope labeled fatty acid with said cells in the presence and the absence of said compound under conditions suitable for incorporation into lipids;
   b. extracting lipids from said cells in a one-step extraction with isopropyl alcohol;
   c. determining the level of a stable isotope labeled triglyceride in the extract obtained from said cells contacted in the presence of said compound;
   d. determining the level of a stable isotope labeled triglyceride in the extract obtained from said cells contacted in the absence of said compound;
   e. comparing the level of the stable isotope labeled triglyceride in the presence of said compound to the level of the stable isotope labeled triglyceride in the absence of said compound; and
   f. selecting a compound for which the level of the stable isotope labeled triglyceride in the presence of said compound is significantly lower than the level of the stable isotope labeled triglyceride in the absence of said compound thereby identifying the compound which inhibits the in vivo activity of DGAT in said cells;
   wherein said stable isotope labeled triglyceride is detected by a liquid chromatographic-mass spectrophotometric system; and
   wherein said cells are differentiated adipocytes or human hepatoma HUH7 cells and the method identifies an inhibitor of DGAT1 activity, or wherein said cells are human breast cancer MCF7 cells and the method identifies an inhibitor of DGAT2 activity.

2. The method of claim 1, wherein said stable isotope is $^{13}C$.

3. The method of claim 1, wherein said stable isotope labeled fatty acid is $^{13}C_{18}$-oleic acid.

4. The method of claim 1, wherein the method further comprises the step of depleting endogenous fatty acids prior to contacting the cells with the isotope labeled fatty acid.

5. The method of claim 4, wherein the step of depleting comprises culturing the cells with charcoal-treated serum or serum-free medium for an appropriate period of time.

6. The method of claim 1, wherein the contacting step comprises incubating the stable isotope labeled fatty acid with the cells in the presence and the absence of said compound for a period of approximately 30 to 120 minutes.

7. The method of claim 1, wherein the steps of determining the level of the stable isotope labeled triglyceride is carried out in the presence of isopropyl alcohol.

8. A high-throughput method for identifying a compound which inhibits the in vivo activity of acyl-coA: diacylglycerol acyltransferase (DGAT) in cells, consisting essentially of the steps of:
   a. depleting endogenous fatty acids present in said cells;
   b. contacting said cells with a stable isotope labeled fatty acid in the presence and the absence of said compound under conditions suitable for incorporation into lipids;
   c. washing said cells;
   d. extracting lipid molecules from said cells in a one-step extraction with isopropyl alcohol;
   e. determining the level of a stable isotope labeled triglyceride in the isopropyl alcohol containing extract obtained from said cells contacted in the presence of said compound, in the presence of isopropyl alcohol;
   f. determining the level of a stable isotope labeled triglyceride in the isopropyl alcohol containing extract obtained from said cells contacted in the absence of said compound, in the presence of isopropyl alcohol;
   g. comparing the level of the stable isotope labeled triglyceride in the presence of said compound to the level of the stable isotope labeled triglyceride in the absence of said compound; and
   h. selecting a compound for which the level of the stable isotope labeled triglyceride in the presence of said compound is significantly lower than the level of the stable isotope labeled triglyceride in the absence of said compound thereby identifying the compound which inhibits the in vivo activity of DGAT in said cells;
   wherein said stable isotope labeled triglyceride is detected by a liquid chromatographic-mass spectrophotometric system; and
   wherein said cells are differentiated adipocytes or human hepatoma HUH7 cells and the method identifies an inhibitor of DGAT1 activity, or wherein said cells are human breast cancer MCF7 cells and the method identifies an inhibitor of DGAT2 activity.

9. A high-throughput method for identifying a compound which inhibits the in vivo activity of acyl-coA: diacylglycerol acyltransferase (DGAT) in cells, consisting essentially of the steps of:
   a. contacting a stable isotope labeled fatty acid with said cells in the presence and the absence of said compound under conditions suitable for incorporation into lipids;
   b. extracting said cells in a one-step extraction with isopropyl alcohol;

c. determining the level of a stable isotope labeled triglyceride in the isopropyl alcohol containing extract obtained from said cells contacted in the presence of said compound;
d. determining the level of a stable isotope labeled triglyceride in the isopropyl alcohol containing extract obtained from said cells contacted in the absence of said compound;
e. comparing the level of the stable isotope labeled triglyceride in the presence of said compound to the level of the stable isotope labeled triglyceride in the absence of said compound; and
f. selecting a compound for which the level of the stable isotope labeled triglyceride in the presence of said compound is significantly lower than the level of the stable isotope labeled triglyceride in the absence of said compound thereby identifying the compound which inhibits the in vivo activity of DGAT in said cells;
wherein said stable isotope labeled triglyceride is detected by a liquid chromatographic-mass spectrophotometric system; and
wherein said cells are differentiated adipocytes or human hepatoma HUH7 cells and the method identifies an inhibitor of DGAT1 activity, or
wherein said cells are human breast cancer MCF7 cells and the method identifies an inhibitor of DGAT2 activity.

* * * * *